United States Patent [19]

Frey et al.

[11] Patent Number: 5,397,440
[45] Date of Patent: Mar. 14, 1995

[54] ISOLATION OF DIMETHYL 4,4'-BIPHENYLDICARBOXYLATE

[75] Inventors: Michael Frey, Neusäss; Ulrich Hertenstein, Gablingen; Rainer Schaller, Wertingen, all of Germany

[73] Assignee: Hoechst Aktiengesellschaft, Frankfurt, Germany

[21] Appl. No.: 227,058

[22] Filed: Apr. 13, 1994

[30] Foreign Application Priority Data

Apr. 16, 1993 [DE] Germany ............. 43 12 491.7

[51] Int. Cl.⁶ .................. B01D 3/10; B01D 9/02; C07C 67/52
[52] U.S. Cl. .................. 203/48; 23/295 R; 203/91; 203/DIG. 16; 560/78
[58] Field of Search ............ 203/48, 63, 91, DIG. 16; 23/295 R; 159/47.1, DIG. 16, DIG. 23; 210/770, 772; 560/78, 77; 562/480, 486, 488

[56] References Cited

U.S. PATENT DOCUMENTS

| 3,227,153 | 10/1966 | Pieroh et al. | 560/77 |
| 3,914,287 | 10/1975 | Takeda | 560/77 |
| 4,683,034 | 7/1987 | Bader et al. | 560/78 |
| 5,116,518 | 5/1992 | Bachmann et al. | 203/48 |

FOREIGN PATENT DOCUMENTS 2310824 1/1973 Germany .
4266851 9/1992 Japan .

OTHER PUBLICATIONS

European Search Report, No. 94105455.3, Jun. 27, 1994.

Primary Examiner—Virginia Manoharan
Attorney, Agent, or Firm—Connolly and Hutz

[57] ABSTRACT

Process for isolating dimethyl 4,4'-biphenyldicarboxylate from residues of DMT production, which includes first distilling the residues at a pressure of at most 7 mbar at a boiler temperature from 200° to 350° C., subsequently treating the distillate which distills over in the range from 230° to 270° C. at a pressure of, for example, 0.2 mbar for from 10 to 60 minutes with 0.7 to 10 times the amount of an organic solvent at a temperature from 70° to 180° C., if required, separating the clear solution from undissolved components, cooling the removed clear solution to a temperature from 45° to 65° C. and allowing it to crystallize at this temperature, resulting in a suspension of dimethyl 4,4'-biphenyldicarboxylate crystals from which the crystals are isolated by washing one or more times with the same or a different solvent and by drying.

10 Claims, No Drawings

ISOLATION OF DIMETHYL 4,4'-BIPHENYLDICARBOXYLATE

DESCRIPTION

The present invention relates to the isolation of dimethyl 4,4'-biphenyldicarboxylate from residues of the preparation of dimethyl terephthalate.

Dimethyl terephthalate (=DMT) is a useful starting material which is prepared on an industrial scale and is used on a large scale for the production of polyester fibers. It is obtained by catalytic oxidation of xylene, reaction of the crude oxidation mixture with methanol and subsequent fractional distillation of the crude dimethyl terephthalate thus prepared. In this distillation, there remains in the distillation boiler a dark viscous residue which has to be disposed of, which has hitherto been preferably carried out by incineration.

Those skilled in the art will know that this residue is a complex mixture of various byproducts of DMT production, which typically contains from 0.5 to 10% by weight of dimethyl 4,4'-biphenyldicarboxylate. Dimethyl 4,4'-biphenyldicarboxylate is also present in similar amounts in other secondary product streams from DMT plants (e.g. distillate from methanolysis).

U.S. Pat. No. 3,277,153 describes a process for isolating methyl esters of biphenylpolycarboxylic acids besides dimethyl 3,4-benzocoumarindicarboxylate from the distillation residues obtained in dimethyl terephthalate production. In this process, a distillation residue from which all terephthalic acid and dimethyl isophthalate has been removed by distillation at reduced pressure is digested in hot methanol or xylene. Insoluble material is removed, the clear solution obtained is freed of solvent and the extracts obtained are worked up in a manner known per se to give chemically uniform substances. This process is extremely complicated, since, as described in said reference, multiple recrystallization from various solvents is required to isolate pure dimethyl 4,4'-biphenyldicarboxylate. Furthermore, the products thus obtained generally contain unwanted residues of oxidation catalyst.

DE-A-23 10 824 describes the isolation of dimethyl 4,4'-biphenyldicarboxylate from residues of DMT production by distillation and crystallization after an obligatory heat treatment. It is emphasized therein that without this heat treatment a large amount of undesired compounds are formed, so that the isolation of pure dimethyl 4,4'-biphenyldicarboxylate is difficult. A very serious disadvantage of this process is that the dimethyl 4,4'-biphenyldicarboxylate thus obtained is contaminated with about 9% by weight of trimethyl 2,4',5-biphenyltricarboxylate. This contamination is extremely deleterious to the preparation of polyesters, since even in traces it leads to branching and crosslinking and thus makes the polymer unusable. This contamination has to be removed by repeated extraction of the product with a solvent, which always requires very imperfect compromise between loss of material and purity.

Dimethyl 4,4'-biphenyldicarboxylate is a useful starting material for syntheses and can, for example, also be used as a modifier in the preparation of polyesters to specifically influence the property profile of these polymers and can thus be used as a starting material for polyesters giving improved properties of the shaped articles produced therefrom, in particular fibers, films or thermoplastically molded parts produced therefrom.

For the preparation of polyesters, it is crucial that raw materials of high purity are used, since otherwise sufficiently high molecular weights cannot be obtained and unwanted branching and crosslinking occurs.

Dimethyl 4,4'-biphenyldicarboxylate and its preparation are known per se. An overview of the formation of preparation of dimethyl 4,4'-biphenyldicarboxylate is given in "Beilsteins Handbuch der organischen Chemie", Volume 9(I), page 927; Volume 9(II), page 665 and Volume 9(III), page 4519. According to this, dimethyl 4,4'-biphenyldicarboxylate is most favorably prepared by a multistage synthesis in which 4,4'-dimethylbiphenyl ("ditolyl") is first oxidized with dichromate/sulfuric acid to give 4-methylbiphenyl-4'-carboxylic acid and this is oxidized with alkaline permanganate solution to give 4,4'-biphenyldicarboxylic acid and this latter compound is esterified with methanol.

It has now been surprisingly found that dimethyl 4,4'-biphenyldicarboxylate can be isolated from the distillation residue formed in the preparation of dimethyl terephthalate and from secondary streams of DMT production.

The present invention accordingly provides a process for isolating dimethyl 4,4'-biphenyldicarboxylate from residues and secondary streams of DMT production, which comprises first distilling the residues or the material of the secondary streams at a pressure of at most 7 mbar, preferably of at most 4 mbar, in particular from 0.2 to 3 mbar, at a boiler temperature from 200° to 350° C., preferably from 200° to 310° C., to obtain a wax-like distillate which passes over at a pressure of, for example, 0.2 mbar in the range from 230° to 270° C. and which contains less than 20% by weight, preferably less than 10% by weight, of residual DMT.

This distillate is subsequently treated for from 10 to 60 minutes with from 0.7 to 10 times, preferably from 1 to 5 times, its weight of an organic solvent, if desired under pressure (i.e. in a closed vessel at the vapor pressure of the solvent established at the treatment temperature), at a temperature of from 70° to 180° C., preferably from 70° to 150° C., particularly at the boiling point of the solvent (at atmospheric pressure). The solution thus obtained is, if required, separated from undissolved, mostly jelly-like, components, for example by decantation, filtration or centrifugation. The clear solution separated off is cooled to a temperature from 45° to 65° C., preferably from 50° to 55° C., and allowed to crystallize at this temperature for from 0.5 to 15 hours, preferably from 0.5 to 8 hours, which results in a suspension of dimethyl 4,4'-biphenyldicarboxylate crystals from which the crystals can be isolated by conventional means. The crystals are advantageously separated off from the suspension by filtration, preferably on pressure or vacuum filters, or by centrifugation. If desired, they are washed one or more times with the same or a different organic solvent, preferably as low-boiling as possible, to completely free the crystals of adsorbed impurities. Subsequently the crystals are dried.

Suitable organic solvents for carrying out the process of the invention are lower alkanols having from 1 to 8, preferably 1–4, carbon atoms, in particular methanol, but also petroleum fractions having a boiling point of about 50°–150° C., such as petroleum ether or ligroin, chlorinated hydrocarbons such as methylene chloride, chloroform, trichloroethylene, perchloroethane or else monochlorobenzene, linear or cyclic ethers such as diethyl ether, tetrahydrofuran or dioxane, lower ketones, such as acetone or methyl ethyl ketone or monocyclic aliphatic or aromatic solvents such as cyclohexane, benzene, toluene or xylenes.

For carrying out the process of the invention, preference is given to using lower alkanols, in particular methanol and ethanol.

The dimethyl 4,4'-biphenyldicarboxylate obtained in this way has a purity of over 99.8% by gas chromatographic analysis and is suitable for the preparation of polyesters without further purification. In particular, the dimethyl 4,4'-biphenyldicarboxylate thus prepared is free of residues of the oxidation catalysts. However, if desired, this dimethyl 4,4'-biphenyldicarboxylate can be further purified, for example to over 99.9%, by recrystallization from suitable solvents such as methanol or xylene.

The process of the invention will now be more particularly described by way of example.

EXAMPLE 1

100 g of the residue obtained in the preparation of dimethyl terephthalate are distilled at $0.2 \cdot 10^{-3}$ bar up to a bath temperature of 300° C. 20.1 g of a yellow wax-like distillate pass over at a temperature from 230° to 270° C.

This distillate is refluxed with 75 ml of methanol for 30 minutes. The methanol solution obtained is decanted off from a jelly-like sediment and is cooled to 50° C. The solution is allowed to crystallize for 1 hour at this temperature, and the crystals formed are filtered off with suction, washed with a small amount of ice-cold methanol and diethyl ether and dried in vacuo.

Yield: 2.5 g of colorless crystals of dimethyl 4,4'-biphenyldicarboxylate having a melting point from 212° to 214° C.

EXAMPLE 2

830 kg of distillation residue from DMT production, containing 1.9% by weight of dimethyl 4,4'-biphenyldicarboxylate and 3% by weight of residual DMT, is distilled at a bath temperature rising from 200° C. to 290° C. in a vacuum of from 1 to 3 mbar, 300 kg of a bright yellow distillate being obtained.

The distillate, which possesses a solidification point of about 110° C., is heated to 90° C. with 300 kg of methanol in a closed vessel under pressure, a clear solution being obtained. This solution is cooled to 55° C. and stirred for 30 minutes at this temperature. The crystals which crystallize out are filtered off, washed twice with 20 l of methanol each time to free them of adhering impurities, and are dried at 50° C. in vacuo.

Yield: 3.9 kg of colorless crystals of dimethyl 4,4'-biphenyldicarboxylate having a melting point of 215° C. The purity (by gas chromatography) is 99.8%.

EXAMPLE 3

276 kg of a distillate, containing 2.8% by weight of dimethyl 4,4'-biphenyldicarboxylate and 7.3% by weight of DMT, are heated to 100° C. with 310 kg of methanol in a closed vessel under pressure, a clear solution being obtained. The solution is cooled to 57° C. and stirred for 60 minutes at this temperature. The crystals which crystallize out are filtered off, washed twice with 20 kg of methanol each time to free them of adhering impurities, and are dried at 50° C. in vacuo.

Yield: 8.2 kg of colorless crystals of dimethyl 4,4'-biphenyldicarboxylate having a melting point of 215° C. The purity (by gas chromatography) is 99.85%.

What is claimed is:

1. A process for isolating dimethyl 4,4'-biphenyldicarboxylate from residues and secondary streams of DMT production, which comprises the steps of
    first, distilling the residues or the material of the secondary streams at a pressure of at most 7 mbar at a boiler temperature from 200° to 350° C. to form a distillate,
    second, treating the distillate for from 10 to 60 minutes with an organic solvent present in an amount by weight of from 0.7 to 10 times the weight of said distillate, at a temperature from 70° to 180° C. to form a solution
    third, cooling the solution to a temperature of from 45° to 65° C. and allowing the solution to crystallize at this temperature, thereby forming a suspension of dimethyl 4,4'-biphenyldicarboxylate.
2. The process as claimed in claim 1, wherein the organic solvent used is an alkanol having from 1 to 8 carbon atoms.
3. The process as claimed in claim 1, wherein the organic solvent used is methanol.
4. The process as claimed in claim 1, wherein distillation is carried out at a boiler temperature from 200° to 310° C.
5. The process as claimed in claim 1, wherein the distillate is treated with from 1 to 5 times its amount of the organic solvent.
6. The process as claimed in claim 1, wherein the treatment of the distillate with the organic solvent is carried out at from 70° to 150° C.
7. The process as claimed in claim 1, which comprises after the step of treating the distillate from 10 to 60 minutes with an organic solvent, the additional step of separating undissolved components from the solution.
8. The process as claimed in claim 1, further comprising the step of isolating the 4,4'-biphenyldicarboxylate crystals from the resulting suspension.
9. The process as claimed in claim 8, further comprising the step of washing the isolated crystals with a solvent.
10. The process as claimed in claim 9, wherein the washed crystals are dried.

* * * * *